United States Patent [19]

Neri

[11] Patent Number: 4,912,554
[45] Date of Patent: Mar. 27, 1990

[54] ELECTROOPTICAL PACKET CONTROL METHOD

[75] Inventor: Armando Neri, Bologna, Italy

[73] Assignee: G. D. Societá Per Azioni, Turin, Italy

[21] Appl. No.: 144,427

[22] Filed: Jan. 15, 1988

[30] Foreign Application Priority Data

Jan. 20, 1987 [IT] Italy ................................ 3322 A/87

[51] Int. Cl.$^4$ ............................................. H04N 7/18
[52] U.S. Cl. .................................... 358/106; 358/107;
209/938; 356/237
[58] Field of Search ....................... 358/101, 106, 107;
356/237, 384, 71; 382/8; 250/592, 223 R, 562;
209/939, 905, 587, 938; 198/339.1, 344, 464.4,
605, 572

[56] References Cited

U.S. PATENT DOCUMENTS

| | | | |
|---|---|---|---|
| 3,049,588 | 8/1962 | Barnett | 358/106 |
| 3,932,042 | 1/1976 | Faani et al. | 358/106 |
| 4,352,430 | 10/1982 | Maier et al. | 358/106 |
| 4,460,273 | 7/1984 | Koizumi et al. | 356/237 |
| 4,672,437 | 6/1987 | Casper | 358/106 |
| 4,706,336 | 11/1987 | Hartmann et al. | 209/938 |
| 4,759,074 | 7/1988 | Iadipaolo et al. | 382/8 |
| 4,764,969 | 8/1988 | Ohtombe et al. | 358/106 |

Primary Examiner—John K. Peng
Attorney, Agent, or Firm—Marshall, O'Toole, Gerstein, Murray & Bicknell

[57] ABSTRACT

An electrooptical packet control method, whereby parallelepiped packets are fed along a given route by two conveyors at least partially offset in relation to each other and cooperating with two opposite faces of the packets. Electrooptical pickup means located along the aforementioned route pick up a given number of faces on each packet as it travels along the first conveyor, and the remaining faces on the packet as it travels along the second conveyor. The resulting images are then compared with a reference image, the outcome of which comparison determines acceptance or rejection of each packet.

11 Claims, 2 Drawing Sheets

ELECTROOPTICAL PACKET CONTROL METHOD

BACKGROUND OF THE INVENTION

The present invention relates to an electrooptical packet control method.

On packing machines, electrooptical devices, usually consisting of telecameras, are known to be employed for controlling the surface finish of the packets produced on the machine; which surface control is usually performed by feeding the packets, on a conveyor belt, between two or more telecameras, which are usually offset in relation to each other.

As the packets are arranged with one face contacting the conveyor belt, obviously, at least one face cannot be controlled. Such a limitation may pose problems in cases requiring not only surface but also accurate dimensional inspection of all the faces on the packet.

SUMMARY OF THE INVENTION

The aim of the present invention is to provide a method of controlling the surface characteristics of a packet, which method provides for overcoming the aforementioned drawback. With this aim in view, according to the present invention, there is provided an electrooptical packet control method, characterised by the fact that it comprises stages consisting in:

successively feeding the said packets along first conveyor means defining a first conveying surface arranged contacting a first portion of each said packet;

successively transferring the said packets on to second conveyor means defining a second conveying surface arranged contacting a second portion of each said packet;

performing, via electrooptical means, a first pickup of part of the outer surface of each said packet as the same travels along the said first conveyor means, and a second pickup of the remaining part of the said outer surface of each said packet as the same travels along the said second conveyor means; and comparing the images obtained in the said two pickup operations by the said electrooptical means with reference images, so as to produce conformance signals for controlling a reject device.

BRIEF DESCRIPTION OF THE DRAWINGS

Two non-limiting embodiments of the present invention will be described by way of example with reference to the accompanying drawings, in which.

DETAILED DESCRIPTION OF THE INVENTION

Figure 1:
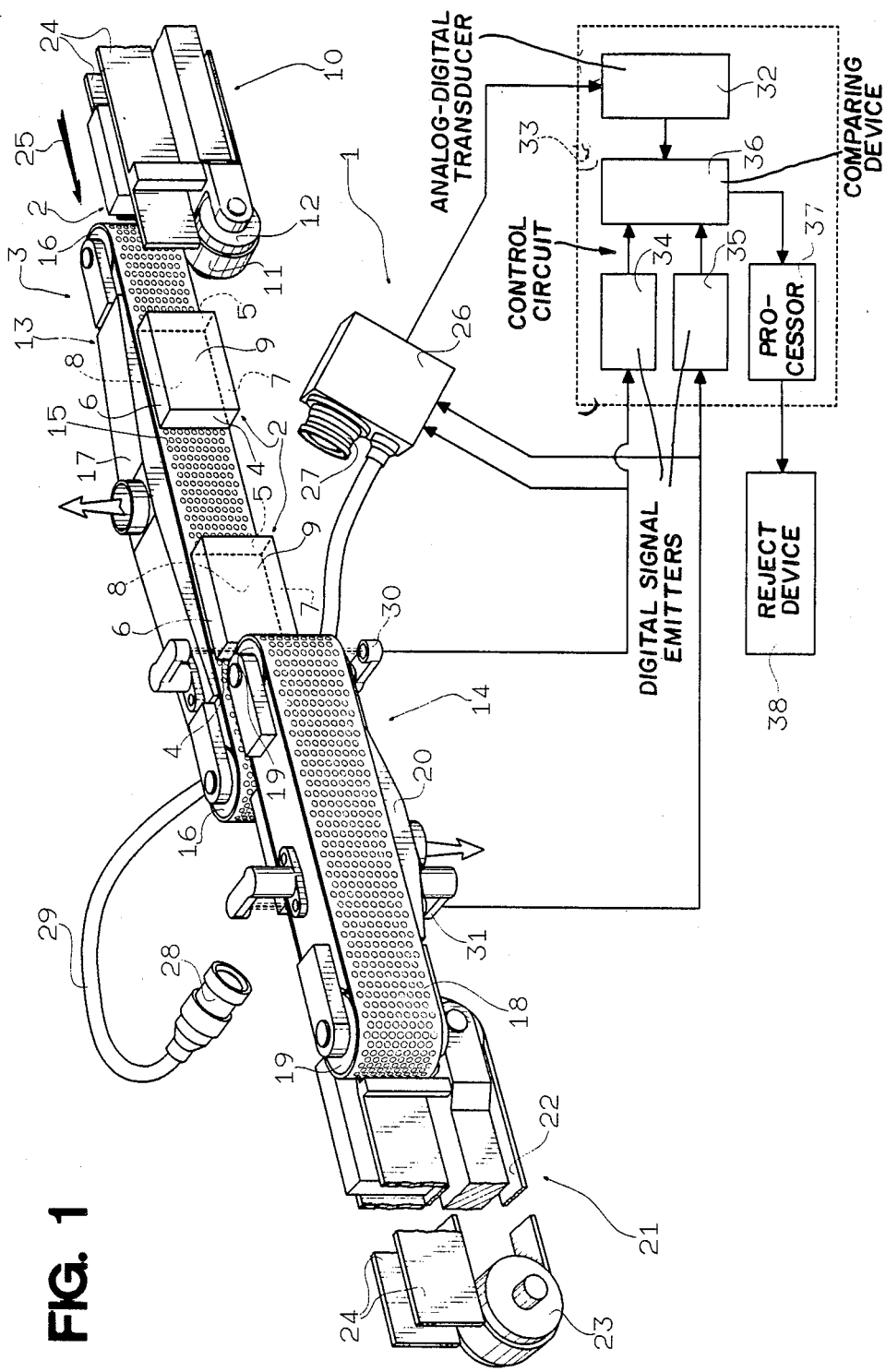
FIG. 1 shows a schematic view in perspective and partial block diagram of a first electrooptical packet control device featuring the method according to the present invention.

Number 1 in FIG. 1 indicates an electrooptical control device for controlling the outer finish, i.e. correct production, of a number of packets 2 fed successively along a given route defined by a conveyor system 3.

Each packet 2 is substantially in the form of a rectangular parallelepipedon having two end faces 4 and 5, a top face 6 and a bottom face 7 parallel with each other, and two side faces 8 and 9 parallel with each other and perpendicular to both faces 4 and 5 and 6 and 7.

Conveyor system 3 comprises an input conveyor 10 consisting of a belt 11 wound about horizontal rollers 12 and arranged contacting the bottom face or portion 7 of packets 2. Conveyor 10 is designed to support and successively feed packets 2 on to a pair of conveyors 13 and 14 designed to support packets 2 by means of suction. Conveyor 13 comprises a belt 15 permeable by air, which is wound about vertical rollers 16 at opposite ends of a suction chamber 17, and which extends contacting side face or portion 8 of packets 2. Conveyor 14 comprises a belt 18 permeable by air, which is wound about vertical rollers 19 at opposite ends of a suction chamber 20, and which extends contacting the side face or portion 9 of packets 2.

Finally, conveyor system 3 comprises an output conveyor 21 aligned with input conveyor 10 and comprising a belt 22 wound about horizontal rollers 23. Both conveyors 10 and 21 present upper guide walls 24 for packets 2. An output end portion of conveyor 10 extends underneath conveyor 13. The conveying portion of belt 15 forming part of the said conveyor 13 replaces the missing end portion of one of walls 24 extending over conveyor 10. Similarly, the two conveyors 13 and 14 partially overlap for a length substantially equal to the length of packet 2 measured in the traveling direction indicated by arrow 25. In particular, the conveying surfaces of belts 15 and 18 are arranged partially facing each other and separated by a distance substantially equal to the thickness of packet 2.

An input end portion of conveyor 21 extends underneath an output portion of conveyor 14. The conveying portion of belt 18 forming part of the said conveyor 14 replaces the missing input portion of one of walls 24 extending over conveyor 21.

Electrooptical device 1 comprises electrooptical telecamera means, in turn, comprising a telecamera 26 located adjacent to conveyor 13 and at such an angle, in relation to the conveying surface of respective belt 15, as to view, via an electrooptical means consisting of lens 27, the three surfaces 5, 7 and 9 of packet 2 located on conveyor 13 in a first given position adjacent to the input end of conveyor 14.

As shown in FIG. 1, telecamera 26 presents a second electrooptical means consisting of lens 28 and connected to telecamera 26 via a fiber bundle 29. Lens 28 is located adjacent to conveyor 14 and at such an angle, in relation to the conveying surface of respective belt 18, as to view the three surfaces 4, 6 and 8 of packet 2 located on conveyor 14 in a second given position adjacent to the output end of conveyor 13.

The arrival of packet 2 into the said first and second positions is detected by respective optical sensors 30 and 31, which activate telecamera 26 so as to enable the same, via lenses 27 and 28, to take two successive shots of the same packet 2 from the said two different angles. As shown in FIG. 1, each time it is activated, telecamera 26 produces an image which, in the form of analog signals, is sent to an analog-digital transducer 32 at the input of a control circuit 33 comprising two digital reference signal emitters 34 and 35 activated respectively by sensors 30 and 31 at the same time as telecamera 26.

Consequently, upon packet 2 moving into the said first control position and being detected by sensor 30, telecamera 26 emits a real image of faces 5, 7 and 9 on packet 2, which image is converted into digital signals by transducer 32, while emitter 34 emits digital signals relative to a reference image.

The digital signals relative to both the said real and reference images are sent simultaneously to a comparing device 36, which detects any differences between the two and supplies the result to a processor 37. On the basis of a given program, processor 37 determines whether or not the surface finish of packet 2 is acceptable, and, if it is not, accordingly controls a known type of reject device 38 located downstream from conveyor 21 and designed to reject the said packet 2 at a later time.

The same process is repeated upon packet 2 moving into the said second control position, wherein sensor 31 simultaneously activates telecamera 26 and image emitter 35, for examining faces 4, 6 and 8 of the said packet 2.

In other words, therefore, each packet 2 is subjected to two successive inspections enabling all the faces of packet 2 to be inspected by virtue of the structure of conveyor system 3.

Figure 2:
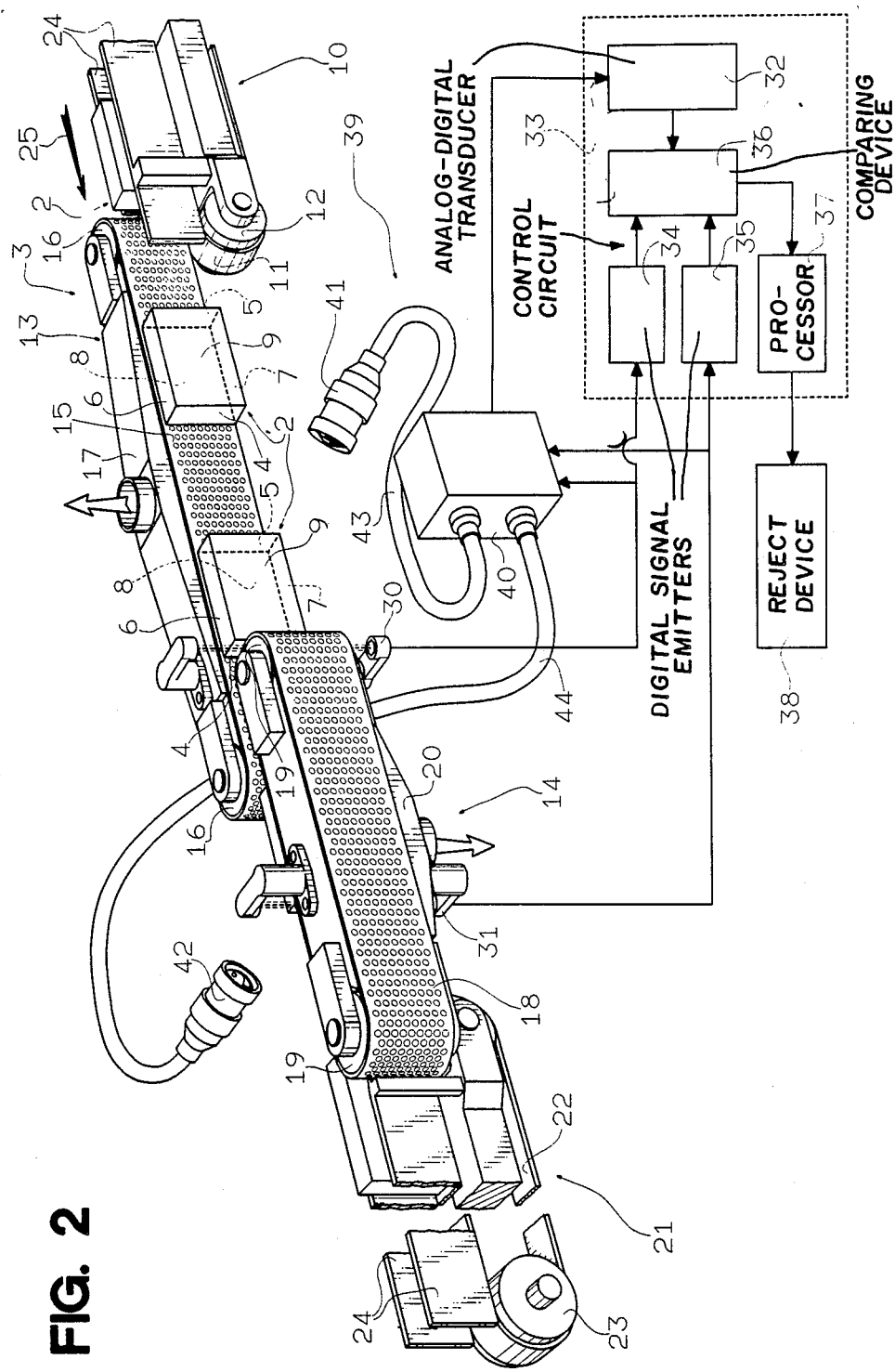
FIG. 2 shows a schematic view in perspective and partial block diagram of a second electrooptical packet control device featuring the method according to the present invention.

According to the FIG. 2 variation, conveyor system 3 presents an electrooptical control device 39 which differs from device 1 solely by comprising an electrooptical telecamera means comprising a telecamera 40, on which the two lenses 41 and 42, corresponding to lenses 27 and 28 on telecamera 26, are connected to telecamera 40 via respective fiber bundles 43 and 44.

I claim:

1. An electrooptical packet control method comprising:
    successively feeding the packets (2) along first conveyor means (13) defining a first conveying surface arranged contacting a first portion of each packet (2);
    successively transferring the packets (2) on to second conveyor means (14) defining a second conveying surface arranged contacting a second portion of each said packet (2);
    performing, via electrooptical means (27, 28 or 41, 42), a first pickup of part of the outer surface of each packet (2) as the same travels along the first conveyor means (13), and a second pickup of the remaining part of the outer surface of each said packet (2) as the same travels along the second conveyor means (14);
    the first and second pickups being performed by transmitting to a single electrooptical telecamera means (26 or 40) a first and second image of each packet (2) viewed from two different angles; and
    comparing the images obtained in the two pickup operations by the electrooptical means (27, 28 or 41, 42) with reference images, so as to produce conformance signals for controlling a reject device (38).

2. A method as claimed in claim 1 in which the two images are transmitted to the single electrooptical telecamera means (26 or 40) using at least one fiber bundle (29 or 43, 44).

3. A method as claimed in claim 1 in which the first and second pickups are performed by electrooptical telecamera means (26 or 40) designed to view the said packets (2) from two different angles.

4. An electrooptical packet control method comprising:
    successively feeding the packets (2) along first conveyor means (13) defining a first conveying surface arranged contacting a first portion of each packet (2);
    successively transferring the packets (2), without rotating the packets, onto second conveyor means (14) defining a second conveying surface arranged contacting a second portion of each packet (2);
    each of the first and second conveyor means having a laterally spaced apart surface with the surfaces being separated from each other a distance substantially equal to the thickness of a packet;
    performing, via electrooptical means (27, 28 or 41, 42), a first pickup of part of the outer surface of each packet (2) as the same travels along the first conveyor means (13), and a second pickup of the remaining part of the outer surface of each packet (2) as the same travels along the second conveyor means (14); and
    comparing the images obtained in the two pickup operations by the electrooptical means (27, 28 or 41, 42) with reference images, so as to produce conformance signals for controlling a reject device (38).

5. A method according to claim 4 in which the first and second conveyor means spaced apart surfaces overlap for a length substantially equal to the length of a packet.

6. A method according to claim 4 in which:
    an input conveyor (10) is aligned to feed packets to the first conveyor means (13) without rotation of the packets; and
    the input conveyor has guide means (24) for guiding packets fed to the first conveyor means (13).

7. A method according to claim 6 in which:
    an output conveyor (21) is aligned to receive packets from the second conveyor means (14) without rotation of the packets; and
    the output conveyor has guide means (24) for guiding packets received from the second conveyor means (14).

8. A method according to claim 4 in which the surfaces of the first and second conveying means have suction means to releasably hold each packet in contact with the respective conveying means surface.

9. A method according to claim 4 in which the first and second pickups are performed by electrooptical telecamera means (26 or 40) designed to view the packets (2) from two different angles.

10. A method according to claim 4 in which the first and second pickups are performed by transmitting to a single electrooptical telecamera means (26 or 40) a first and second image of each said packet (2) viewed from two different angles.

11. A method according to claim 10 in which the two images are transmitted to the single electrooptical telecamera means (26 or 40) using at least one fiber bundle (29 or 43, 44).

* * * * *

UNITED STATES PATENT AND TRADEMARK OFFICE
CERTIFICATE OF CORRECTION

PATENT NO. : 4,912,554

DATED : March 27, 1990

INVENTOR(S) : ARMANDO NERI

It is certified that error appears in the above-identified patent and that said Letters Patent is hereby corrected as shown below:

On the patent face sheet, in item [73] change "Turin" to -- Bologna --.

Signed and Sealed this

First Day of October, 1991

*Attest:*

HARRY F. MANBECK, JR.

*Attesting Officer*      *Commissioner of Patents and Trademarks*